Figure 1:
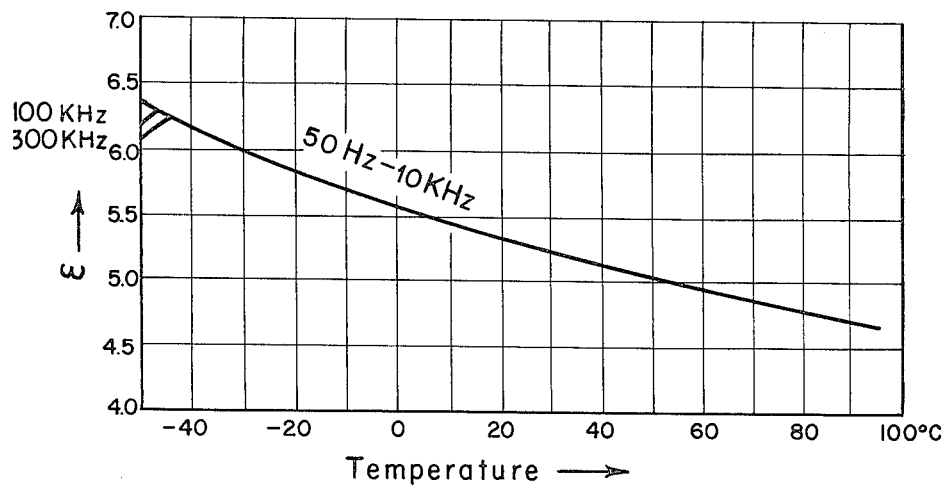

United States Patent [19]

Mathais et al.

[11] 4,438,027
[45] Mar. 20, 1984

[54] CHLORINATED ALKYLAROMATIC BASED COMPOUNDS AND NEW LIQUID DIELECTRICS

[75] Inventors: Henri Mathais, Jarrie; Raymond Commandeur, Vizille, both of France; Achille Pontoglio; Sergio Nebel, both of Brescia, Italy

[73] Assignee: PCUK Produits Chimiques Ugine Kuhlmann, Paris, France

[21] Appl. No.: 429,082

[22] Filed: Sep. 30, 1982

Related U.S. Application Data

[63] Continuation of Ser. No. 243,143, Mar. 12, 1981, abandoned, which is a continuation of Ser. No. 57,982, Jul. 16, 1979, abandoned.

[30] Foreign Application Priority Data

Jul. 27, 1978 [FR] France ............................ 78 22216
Feb. 20, 1979 [FR] France ............................ 79 04259

[51] Int. Cl.$^3$ .............................................. H01B 3/24
[52] U.S. Cl. ........................................... 252/581; 361/317; 570/184; 570/199
[58] Field of Search ............... 252/78.1, 581; 570/184, 570/199; 361/317

[56] References Cited

U.S. PATENT DOCUMENTS

| | | | |
|---|---|---|---|
| 1,931,373 | 10/1933 | Clark | 252/581 |
| 1,944,730 | 1/1934 | Clark | 252/581 |
| 2,012,302 | 8/1935 | Clark et al. | 570/184 |
| 2,233,404 | 3/1941 | Dreisbach | 252/581 |
| 2,244,284 | 6/1941 | Britton et al. | 252/581 X |
| 2,600,691 | 6/1952 | Ross et al. | 570/184 |
| 2,623,910 | 12/1952 | Robinson | 570/184 |
| 3,006,972 | 10/1961 | Fields et al. | 570/184 |
| 3,290,253 | 12/1966 | Blake et al. | 252/78 |
| 3,362,908 | 1/1968 | Polito | 252/581 X |
| 4,260,506 | 4/1981 | Munch et al. | 252/78.1 |

FOREIGN PATENT DOCUMENTS 626317 7/1949 United Kingdom .
1504655 3/1978 United Kingdom .

*Primary Examiner*—P. E. Willis, Jr.
*Attorney, Agent, or Firm*—Pennie & Edmonds

[57] ABSTRACT

New compounds of the formula:

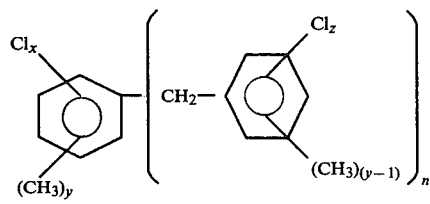

where n, x, y and z have value 1 or 2, their process of preparation and their use as dielectrics such as insulating fluids for transformers alone or in mixture with one or more products of general formula:

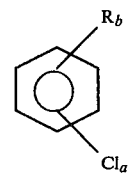

where a varies from 2 to 4, b varies from 0 to 2 and R is an aliphatic hydrocarbon radical containing from 1 to 3 carbon atoms.

9 Claims, 8 Drawing Figures

CHLORINATED ALKYLAROMATIC BASED COMPOUNDS AND NEW LIQUID DIELECTRICS

This is a continuation of application Ser. No. 243,143, filed Mar. 12, 1981, which application is a continuation of application Ser. No. 057,982, filed July 16, 1979, both abandoned.

TECHNICAL FIELD

This invention concerns new chlorinated alkylaromatic based compounds useful as dielectrics.

BACKGROUND ART

Polychlorobiphenol-base products have heretofore been widely used in the field of insulation of electrical equipment, for, aside from their electrical properties, they combine a number of advantages making them very well suited for use as dielectric liquids: very great stability at high temperature and under hydrolysis, little or no flammability, low vapor pressure and moderate price. On the other hand, their absence of biodegradability leads to their accumulation in the environment, which considerably restricts their range of application and has prompted some countries to prohibit them totally or partially. Furthermore, at very low temperature, their dielectric properties drop rapidly, making them difficult to use under conditions of extreme cold.

Other products have also been proposed as dielectric liquids, e.g., the esters described in French Pat. No. 2,322,435, but those esters are readily combustible. As for the polychloropolyphenylalkanes described in French Pat. No. 2,273,351, they are made from alkane dihalides, e.g., dichloro-1-1-ethane, which on the economic level offers no advantage.

DISCLOSURE OF INVENTION

The applicants discovered that it was possible to obtain from a simple and inexpensive raw material—chlorotoluenes or chloroxylenes—products not possessing the biphenyl nucleus and having properties enabling them to be substituted advantageously for polychlorobiphenyls in their dielectric applications without presenting the disadvantages of same. In fact, the absence of biphenyl nuclei and the presence of alkyl groups on the aromatic nuclei has a favorable effect on biodegradability (see in this connection the article by G. Sundstrom. K. Olie and O. Hutzinger, Chemosphere No. 213, pages 103–109, 1977).

It was further discovered that these products have, by comparison with the chlorobiphenyls, greatly improved electrical properties at very low temperatures, which makes them particularly useful under extreme conditions.

The compounds have also been found to have a high dipolar moment and good chemical stability, when the products are subjected to chemical treatments or to the action of an intense electric field. The products also have good flame or fire resistance, which makes them constituents of choice for insulating fluids usable, in particular, for transformers.

The products have a high dielectric constant (or permittivity) over a wide temperature range covering the normal range of use of dielectric liquids and a very low loss factor.

The products according to the invention can be represented by the following general formula:

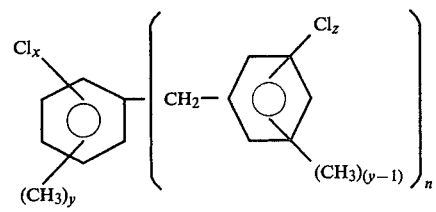

in which $n=1$ or 2 or more, z and $x=1$ or 2, and $y=1$ or 2. When $y=1$, chlorotoluenes are involved, and $y=2$ corresponds to the use of chloroxylenes.

The products are prepared from an isomer of chlorotoluene or chloroxylene or from mixtures thereof by subjecting the isomers to chlorination initiated in standard fashion, that is, either photochemically or in the presence of an initiator, giving rise to free radicals. This reaction can be made at temperatures ranging between about 0° and 150° C. and preferably between about 20° and 100° C. A Friedel-Crafts catalyst, e.g., AlCl$_3$, AlBr$_3$, FeCl$_3$, is then added to the mixture thus obtained. A condensation is produced between the chlorobenzyl or methylchlorobenzyl chlorides formed and the excess chlorotoluenes or chloroxylenes according to the following reaction:

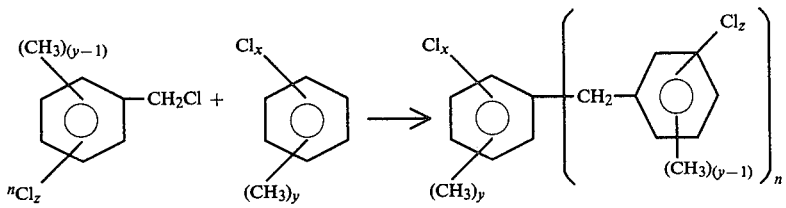

where n, x, y and z have the values assigned above.

This reaction can be carried out at between 20° and 100° C. and, depending on the excess of chlorotoluenes or chloroxylenes present, the proportion of product in which $n=1$ is comparatively great, a large excess of chlorotoluenes or chloroxylenes favoring the obtaining of a product where $n=1$. After destruction of the catalyst and washing of the organic phase, the mixture is subjected to a distillation and chlorotoluenes or chloroxylenes not having reacted are recovered and can be recycled in a subsequent operation. The mixture of product where $n=1$ or 2 is then separated by distillation.

Of course, the crude compounds of the reaction should undergo a preliminary purification treatment with alkaline agents (NaOH, Na$_2$CO$_3$, NaHCO$_3$ or similar calcium or potassium compounds) at a temperature that can range from 20° to 350° C., preferably between 200° and 250° C., for a period varying with the temperature chosen. Sometimes a further distillation can be advantageous.

After that preliminary treatment, a purification phase can follow using fuller's earth or activated alumina, either alone or in mixture, according to the specific techniques known in the field of dielectric liquids.

It can likewise be advantageous to add stabilizers such as epoxide type stabilizers or other type stabilizers such as tetraphenyl tin or anthraquinone compounds.

These stabilizers are generally hydrochloric acid acceptors and are added in variable quantities between 0.001 and 10% and preferably between 0.01 and 0.3%.

Furthermore, if the dielectric liquid is used as insulating fluid for transformers, it is possible and sometimes important to mix it, without detriment to its good qualities, with products having the following general formula:

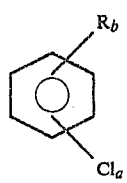

where $a=2$ to 4, $b=0$ to 2 and R is an aliphatic hydrocarbon radical having 1 to 3 carbon atoms.

Among the products responding to that general formula, trichloro or tetrachlorobenzenes, having a rather limited vapor pressure, are commonly used. These products can be introduced at the rate of 30% and up to 60% by weight of mixture.

The following examples illustrate the invention, without, however, limiting it:

EXAMPLE 1

5,080 g of orthochlorotoluene (40 moles) are placed in a 6-liter reactor equipped with stirrer, chlorine feed tube and Philips TLADK 30 W actinic lamp. 568 g of chlorine gas (8 moles) are introduced in 4 hours, keeping the temperature at 70° C. The reaction product is then drawn off the reactor, except for 100 ml in which 16 g of $FeCl_3$ are added. The drawn-off product is then added over a period of 2 hours, keeping the temperature at 30° C. At the end of the reaction, heating is continued for 15 minutes at 100° C. The product obtained is washed, while stirring, with 1 liter of 10% aqueous hydrochloric acid and then twice with one liter of water. The organic phase thus obtained is distilled under a vacuum of 15 mm of mercury up to a maximum temperature of 200° C. at the base. One recovers a first fraction of 2,950 g of orthochlorotoluene, which distills toward 45° C. A second fraction (product A) distilling at 200° C. and representing 1,320 g constitutes the product of the general formula where $n=1$. By lowering the presence of 0.1 mm of mercury, a second fraction of 480 g (product B) is obtained, which distills at between 210° and 245° C. and constitutes the product where $n=2$. There remain in the flask 140 g of heavy products where $n>2$.

Product A possesses the following characteristics:
Specific gravity (20° C.)=1.21
Viscosity (20° C.)=15.17 cst
Refraction index=1.595
Freezing point=$<-50°$ C.
Chlorine content=28.1% (theory 28.3%)

This product A is then purified by addition of 2% by weight $Na_2CO_3$ and heating for 4 hours at 200° C. and is then distilled under 15 mm of mercury of that temperature.

Product A, after the treatment customarily applied to dielectric products (contact with activated alumina and filtration), has 0.1% tetraphenyl tin, a standard stabilizer of dielectric products, added to it. Its dielectric constant $\epsilon$ was measured according to the ASTM D 924 standard at different temperatures and for different frequencies, which led to the curve of FIG. 1. By way of comparison, the same measurement was taken on a trichlorobiphenyl treated in the same way. The result is given in the curve of FIG. 2. For the trichlorobiphenyl, a drop in the value of $\epsilon$ is observed from $-10°$ C. under 300 KHz. For product A, this drop is apparent only from $-50°$ C. under 300 KHz.

Figure 3:
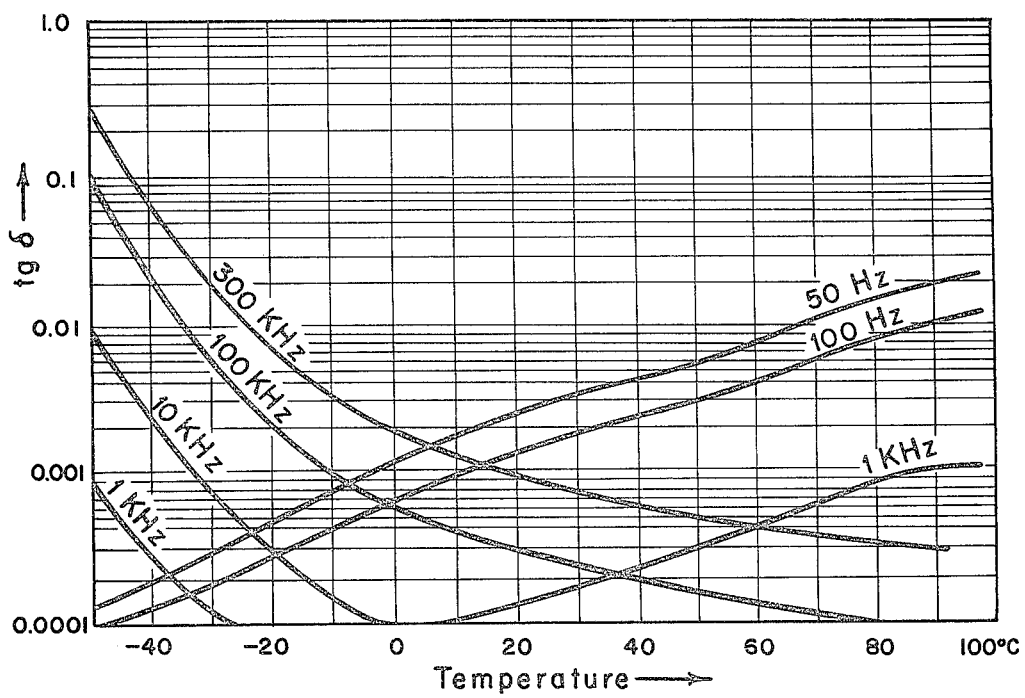
Figure 4:
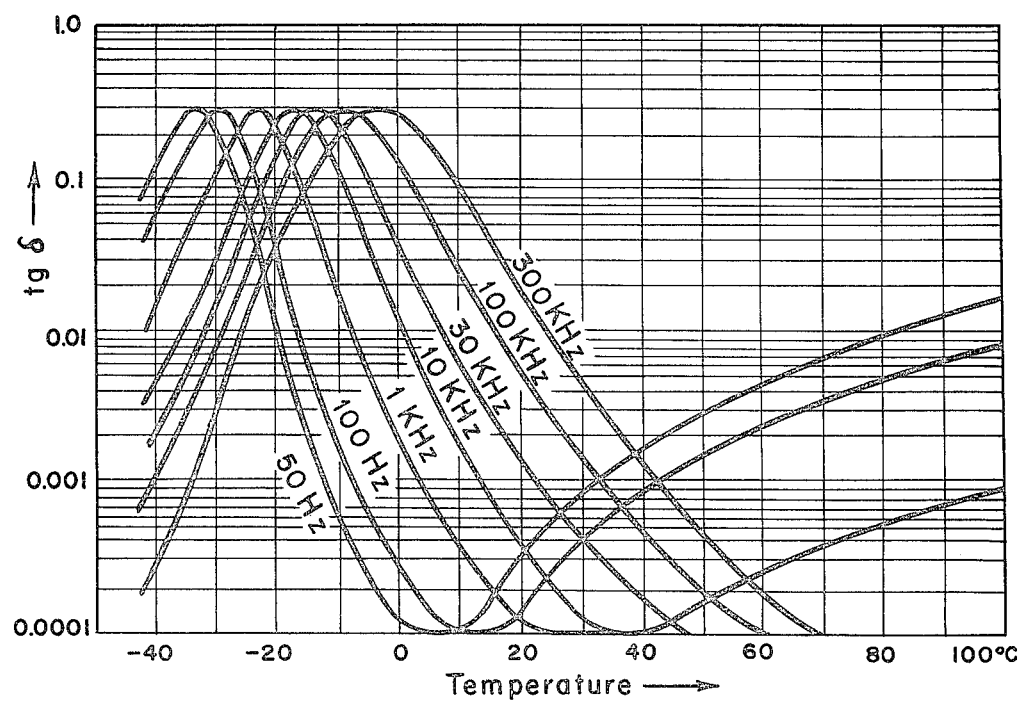

Comparison of the course of the loss factor (tg $\delta$) (FIGS. 2 and 4) (measurement according to the ASTM D 924 standard) as a function of temperature for different frequencies again reveals a substantial difference in behavior of product A (FIG. 3) from the trichlorobiphenyl (FIG. 4). The set of curves is shifted toward low temperatures for product A. Thus, for a frequency of 50 Hz, the loss factor shows a rapid rise from $-10°$ C. for the trichlorobiphenyl, while in the case of product A, the minimum is not even reached for $-50°$ C.

Other properties of product A are very close to those of the trichlorobiphenyl, as the following table shows:

|  | Product A | Trichlorobiphenyl |
|---|---|---|
| Softening point (ASTM D 7) | $<-50°$ C. | $-20°$ C. |
| Viscosity at 20° C. | 15.17 cst | 65 cst |
| Resistivity at 90° C. (ASTM D 1169) | $7.4 \cdot 10^{12}$ ohm · cm | $10^{12}$ ohm · cm |
| Dielectric strength (VDE O 370) | 320 KV × cm | 200 KV × cm |
| Fire point | none | none |
| Flash point | 178° C. | 205° C. |

EXAMPLE 2

The same procedure as set forth in Example 1 is followed, but replacing the orthochlorotoluene with a mixture of dichlorotoluene isomers. After photochemical chlorination and condensation on the excess dichlorotoluene, distillation leads to a principal fraction distilling at between 230° and 255° C. under 13 mm of mercury and consisting of a mixture of isomers corresponding to the general formula with $n=1$ and $x=z=2$. The product thus prepared has a specific gravity at 20° C. of 1.372 and a chlorine content of 43.9% (theory=44.4%).

EXAMPLE 3

The same procedure as set forth in Example 1 is followed, but replacing the orthochlorotoluene with parachlorotoluene. After reaction, a principal fraction ranging from 200° and 225° C. under 21 mm of mercury is obtained by distillation. That product is a mixture of isomers predominantly having the general formula where $n=1$ and $x=z=1$. Its specific gravity at 20° C. is 1.207 and its chlorine content 28% (theory=28.3%).

A second distillation fraction ranging between 200° and 250° C. under 0.1 mm of mercury corresponds to the general formula where $n=2$ and $x=z=1$.

EXAMPLE 4

The same procedure as set forth in Example 1 is followed, but replacing orthochlorotoluene by a mixture of 50% with orthochlorotoluene and 50% parachlorotoluene. After reaction, distillation at between 200° and 230° C. under 20 mm produces a mixture of isomers corresponding predominantly to the general formula where n=1, x=z=1. The specific gravity of that product is 1.207 and its chlorine content is 27.9% (theory=28.3%). The freezing point is below −25° C. A second fraction, distilling at between 200° and 270° C. under 0.1 mm of mercury, corresponds to the general formula where n=2 and x=z=1.

EXAMPLE 5

6.8 kg of dichlorotoluenes (obtained by limited chlorination of toluene in the presence of $FeCl_3$ at 50° C.) are placed in a reactor equipped with a stirrer, a cooling and heating device and a device for introduction of chlorine, a device for liberation of hydrochloric acid through a condenser and an actinic lamp. The temperature is brought to 80° C. and chlorine is introduced at the rate of 100 g/h. At the end of five hours, the reaction is stopped. The mixture is degassed with nitrogen and transferred into a separating funnel, except for approximately 500 ml in which 16 g of $FeCl_3$ are added. The product drawn off is then reintroduced into the reactor over a period of 2 hours, keeping the temperature at 80°–100° C. An abundant liberation of hydrochloric acid is produced. The temperature is maintained for 2 extra hours. The mixture obtained is washed with hot and then cold water and the excess dichlorotoluenes are distilled on a 30-plate column under a pressure of 250 mm Hg, which is then lowered to 10 mm Hg. A fraction of 2,240 g of product of boiling points ranging between 210° and 240° C. is isolated. That product contains 44.3% chlorine and corresponds to the formula:

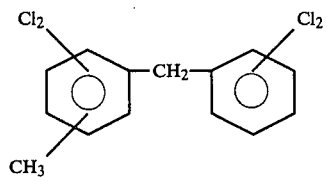

One adds to the fraction thus collected, 1,833 g (i.e., 45% of the mixture obtained) of industrial trichlorobenzene consisting of a mixture of the following isomers:

1,2,3-trichlorobenzene 63%
1,2,4-trichlorobenzene 36%
tetrachlorobenzene 1%

Four grams of tetraphenyl tin are added. After standard dielectric purification by successive treatments on activated alumina, the physical and dielectric properties of the mixture are measured, which are compared with those of a mixture of 70% Askarel (standard polychlorobiphenyl mixture) and 30% trichlorobenzene.

| | Mixture according to example | Askarel type D |
|---|---|---|
| Specific gravity at 20° C. | 1.409 | |
| Softening points | <−55° C. | <−35° C. |
| Viscosity at 20° C. | 8.1 cst | 18–20 cst |
| Flash point | 130–145° C. | 130–145° C. |
| Fire point | none | none |
| Dielectric strength | 280 KV/cm | >200 KV/cm |
| Resistivity (500 V) (90° C.) | $10^{12} \Omega \times cm$ | $>10^{12} \Omega \times cm$ |
| Tg δ × 100 (90°–50 Hz) | <5 | <2 |
| Dielectric constant (90°–50 Hz) | 4.4 | 4.0 to 4.1 |

Figure 5:
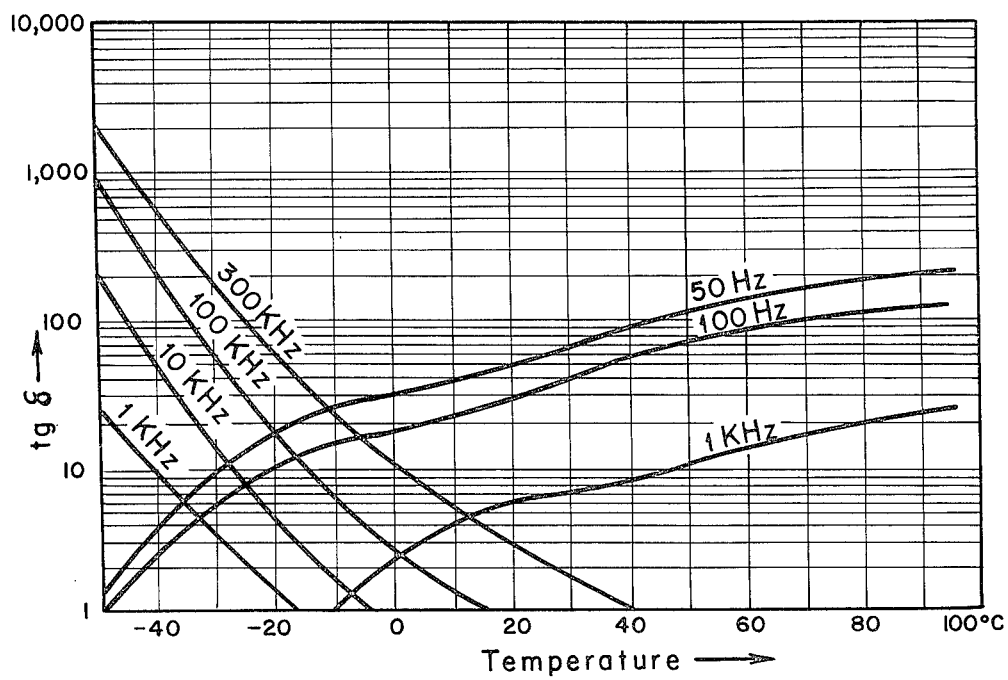
Figure 6:
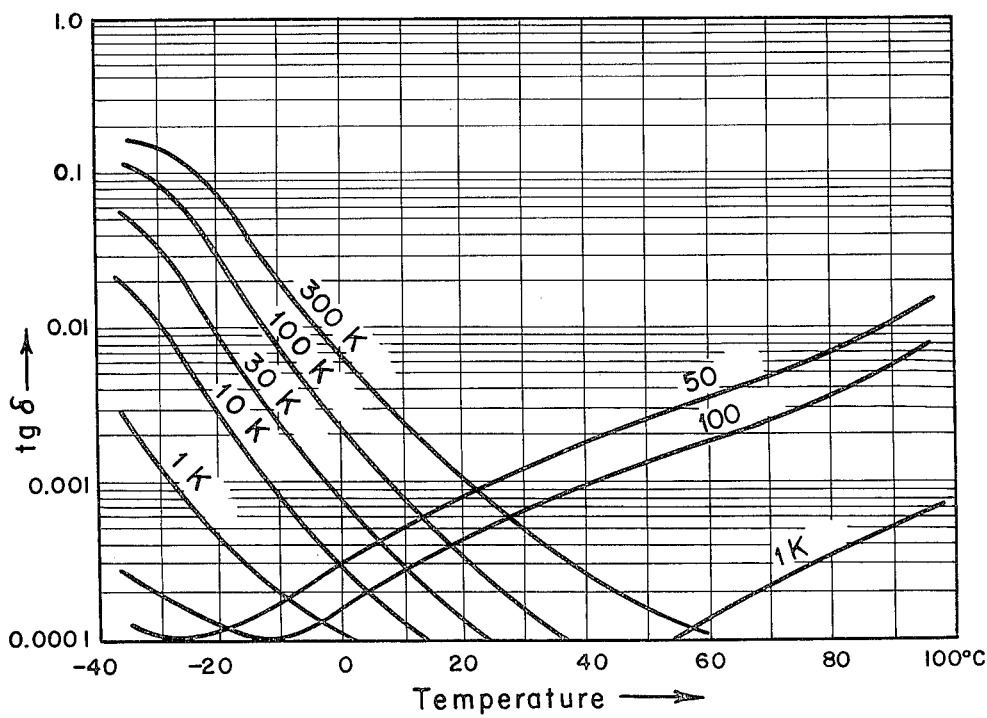
Figure 7:
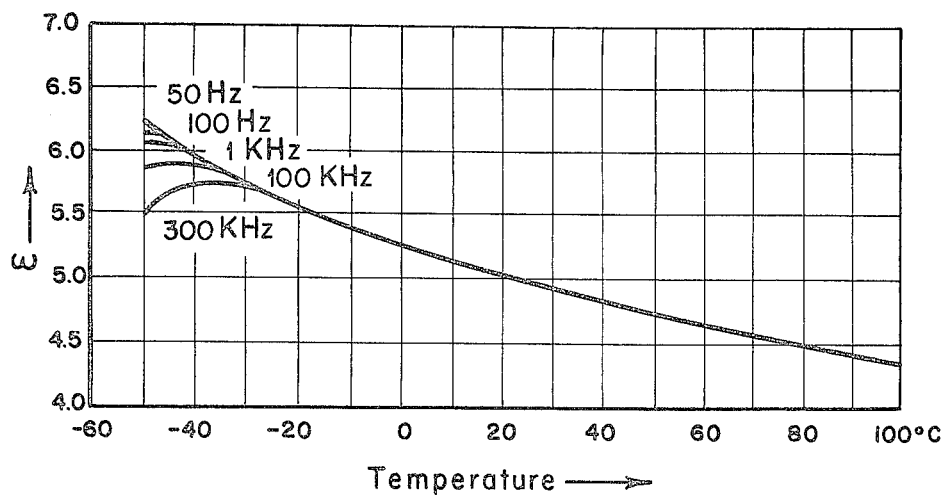
Figure 8:
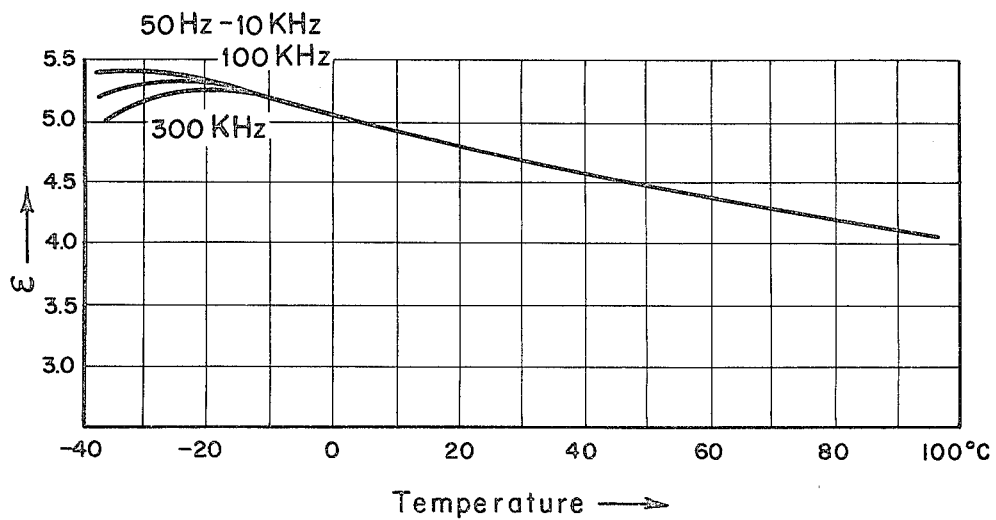

FIGS. 5 and 6 show the differences between the mixture obtained in this example and Askarel type D with regard to the loss factor as a function of temperature and frequency and FIGS. 7 and 8 the differences between the dielectric constants as far as the same products are concerned.

We claim:

1. Liquid dielectrics of formula:

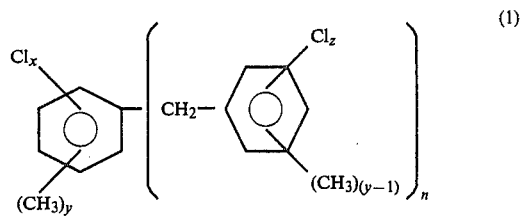

where n, x, y and z have value 1 or 2.

2. Process for the preparation of the liquid dielectric of claim 1 comprising chlorinating a chlorotoluene or chloroxylene or mixture thereof at a temperature between about 0° C. and 150° C. for a sufficient time to produce free radicals; condensing the chlorinated product and excess chlorotoluene or chloroxylene in the presence of a catalyst at a temperature between about 20° C. and 100° C.; and recovering a liquid dielectric.

3. Process according to claim 2, in which the excess chlorotoluenes and/or chloroxylenes unconverted in the chlorination stage are 0.4 to 40 times greater than the quantity of chlorobenzyl or methylchlorobenzyl chlorides obtained.

4. An insulating fluid comprising one or more compounds according to the formula of claim 1 in admixture with one or more compounds of the general formula:

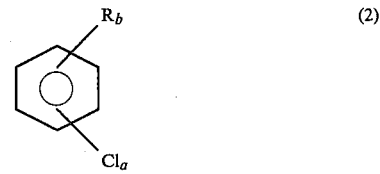

in which a varies from 2 to 4, b varies from 0 to 2 and R is an aliphatic hydrocarbon radical containing 1 to 3 carbon atoms and an acid acceptor.

5. The insulating fluids of claim 4 in which the acid acceptor is an epoxide type or tetraphenyl tin in an amount ranging from between about 0.001 and 10 percent.

6. The insulating fluids of claims 4 or 5 in which the compounds according to the formula of claim 1 constitute about 20 to 80 percent of the mixture.

7. The insulating fluids of claims 4 or 5 where the compound of claim 1 is

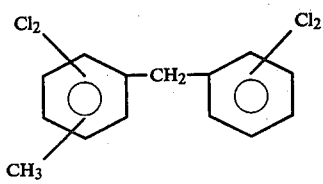

admixed with industrial trichlorobenzene and in which the compound constitutes 40 to 70 percent of the mixture.

8. The insulating fluids of claim 7 in which the trichlorobenzene has the following composition; isomer 1-2-4, 50 to 85 percent, and isomer 1-2-3, 50 to 15 percent.

9. A transformer or condenser containing at least one dielectric compound according to the formula of claim 1 as an insulating fluid.

* * * * *

UNITED STATES PATENT AND TRADEMARK OFFICE
CERTIFICATE OF CORRECTION

PATENT NO. : 4,438,027
DATED : March 20, 1984
INVENTOR(S) : Henri Mathais, Raymond Commandeur, Achille Pontoglio and Sergio Nebel It is certified that error appears in the above—identified patent and that said Letters Patent is hereby corrected as shown below:

Column 3, lines 55-56, reads "presence of", should read --pressure to--.

Figure 2:
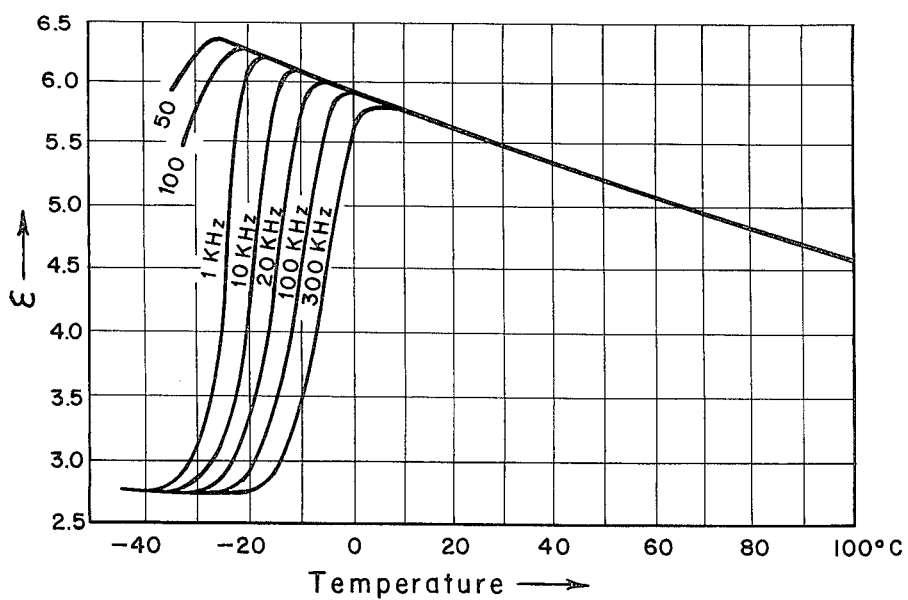

Column 4, line 17, reads "Figs. 2 and 4", should read --Figs. 3 and 4--.

Signed and Sealed this

Eleventh Day of September 1984

[SEAL]

Attest:

GERALD J. MOSSINGHOFF

Attesting Officer

Commissioner of Patents and Trademarks